United States Patent
Ohno et al.

(10) Patent No.: US 11,963,492 B2
(45) Date of Patent: *Apr. 23, 2024

(54) AGENT FOR INCREASING A PLANT FUNCTIONAL COMPONENT CONTENT AND A METHOD FOR MANUFACTURING THE SAME

(71) Applicant: IBIDEN CO., LTD., Gifu (JP)

(72) Inventors: Katsuya Ohno, Gifu (JP); Tomohiro Nohara, Gifu (JP)

(73) Assignee: IBIDEN CO., LTD., Gifu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,886

(22) Filed: Mar. 29, 2022

(65) Prior Publication Data

US 2022/0217913 A1  Jul. 14, 2022

Related U.S. Application Data

(63) Continuation of application No. 16/493,036, filed as application No. PCT/JP2018/008632 on Mar. 6, 2018, now Pat. No. 11,317,568.

(30) Foreign Application Priority Data

Mar. 14, 2017 (JP) ................................ 2017-048723

(51) Int. Cl.
  *A01G 7/06* (2006.01)
  *C05F 11/08* (2006.01)
  *C12P 1/04* (2006.01)

(52) U.S. Cl.
  CPC ............... *A01G 7/06* (2013.01); *C05F 11/08* (2013.01); *C12P 1/04* (2013.01)

(58) Field of Classification Search
  None
  See application file for complete search history.

(56) References Cited

U.S. PATENT DOCUMENTS

| | | | |
|---|---|---|---|
| 11,317,568 B2 * | 5/2022 | Ohno | ....................... A01G 7/06 |
| 2019/0008158 A1 | 1/2019 | Von Maltzahn | |
| 2019/0309248 A1 | 10/2019 | Alibek et al. | |

FOREIGN PATENT DOCUMENTS

| | | | |
|---|---|---|---|
| CN | 101167480 A | 4/2008 | |
| CN | 104178537 A | 12/2014 | |
| EP | 3015543 A1 | 5/2016 | |
| EP | 3510868 A1 | 7/2019 | |
| IN | 201917009245 | 3/2019 | |
| WO | 2012133130 A1 | 10/2012 | |

OTHER PUBLICATIONS

International Search Report, International Application No. PCT/JP2018/008632, dated May 29, 2018, 2 pages.
Translation of the International Preliminary Report on Patentability, application No. PCT/JP2018/008632, dated Sep. 26, 2019, 6 pages.
Extended European Search Report from EP App. No. 18767036.9, dated Dec. 15, 2020 (8 pages).
Office Action from Indian Patent Application No. 201937038114, dated May 19, 2021 (6 pages).
Office Action from Japanese Patent Application No. 2019-505912 and English Translation, dated Aug. 4, 2020 (8 pages).
Nie et al., "A Novel Paradigm of Fatty Acid [beta]-Oxidation Exemplified by the Thioesterase-Dependent Partial Degradation of Conjugated Linoleic Acid That Fully Supports Growth of *Escherichia coli*", 47 Biochemistry 9618, Aug. 15, 2008 (9 pages).
Ohno et al., "Approach of Plant Responses to Plant Disease Control by Bacterial Metabolites of Fatty Acid (BMFA)", Lexture Nos. 3J32p07-3J32p10, http://www.jsbba.or.jp/MeetingofJSBBA/2017/meeting_of_jsbba_2017.html, Mar. 5, 2017 (10 pages).
Silliker et al. "Studies on the Aerobic Oxidation of Fatty Acids by Bacteria", 61 J. Bacteriology 653-659, https://ib.asm.org/content/jb/61/6/653,full.pdf, Feb. 24, 1951 (7 pages).
Ohno et al., "Promotion of plant growth and behavior of plant metabolism components by bacterial fatty acid metabolites (BMFA)", Regulation of Plant Growth & Development, Oct. 6, 2017 (5 pages).

(Continued)

*Primary Examiner* — Wayne A Langel
(74) *Attorney, Agent, or Firm* — Ware, Fressola, Maguire & Barber LLP

(57) ABSTRACT

The objective of the invention is to provide an agent for increasing a plant functional component content, which is capable of increasing a content of the plant functional component by being adequately sprayed to the plant or injected into the soil without using stress cultivation conditions or plants with high content of functional component, and a method for manufacturing the same. An agent for increasing a plant functional component content comprising a fatty acid metabolite obtainable by a metabolism of a fatty acid with 4-30 carbon atoms by proteobacteria under a dissolved oxygen concentration of 0.1-8 mg/L, and a method for manufacturing an agent for increasing a plant functional component content comprising a fatty acid metabolite, comprising a step for a fatty acid metabolism wherein a fatty acid with 4-30 carbon atoms is subjected to a proteobacterial metabolization under a dissolved oxygen concentration of 0.1-8 mg/L.

20 Claims, 2 Drawing Sheets

(56) References Cited

OTHER PUBLICATIONS

Ohno et al., "Promotion of plant growth and behavior of plant metabolism components by bacterial fatty acid metabolites (BMFA)", Abstracts of the Annual Meetings Japanese Society of Soil, Science and Plant Nutrition, Sep. 5, 2017 (5 pages).

Lumen "Proteobacteria", accessed from www.courses.lumenlearning.com (Year: 2020).

Water-on-the-Web, "DO-% Saturation Calculator", accessed from www.waterontheweb.org (Year: 2020).

* cited by examiner

AGENT FOR INCREASING A PLANT FUNCTIONAL COMPONENT CONTENT AND A METHOD FOR MANUFACTURING THE SAME

TECHNICAL FIELD

The present invention relates to an agent for increasing a plant functional component content and a method for manufacturing an agent for increasing a plant functional component content.

BACKGROUND ART

Many plants contain a various group of functional components such as vitamins, carotenoid, polyphenols. Recently the interest in those functional components contained in agricultural plants has been growing due to the health trends, and especially there is a strong need for the plant which contains a high amount of plant functional components exhibiting an antioxidant activity to remove the radicals, such as active oxygen, which are considered to damage cells and tissues and contribute to develop cancer or lifestyle-related disease or to promote aging. Therefore, many attempts have been made to significantly increase a production of the beneficial functional components in plants.

For a method to increase a yield of functional components contained in plants, a technique to increase an amount of the polyphenol contained in strawberry fruits by irradiating UV light is described in Reference 1.

PRIOR ART DOCUMENT

Patent Document

Patent Document 1: WO 2012/133130

SUMMARY OF THE INVENTION

Problem to be Solved by the Invention

However, UV irradiation to the plant may damage a plant living tissue, so that the irradiation time was limited. Further, since there is a concern that UV irradiation may damage a human body, it involved a problem that the operator's safety was not secured sufficiently.

The present invention has been made in view of such circumstances as mentioned above, and an object of the present invention is to provide an agent for increasing a plant functional component content which is capable of safely increasing a content of the plant functional component by being adequately sprayed to the plant or injected into the soil without causing any adverse effect on the plant living tissue, and a method for manufacturing the same.

Means to Solve the Problem

The present invention relates to an agent for increasing a plant functional component content comprising a fatty acid metabolite obtainable by a metabolism of a fatty acid with 4 to 30 carbon atoms by proteobacteria under a dissolved oxygen concentration of 0.1 to 8 mg/L.

It may be preferable for the agent for increasing a plant functional component content that the fatty acid is a liquid fatty acid at a temperature of 20° C.

It may be preferable for the agent for increasing a plant functional component content that the metabolism is a metabolism in the presence of at least one type of mineral selected from Mg, P, Na and K.

It may be preferable for the agent for increasing a plant functional component content that the proteobacteria are pre-cultured proteobacteria.

It may be preferable for the agent for increasing a plant functional component content that the pre-cultured proteobacteria are proteobacteria pre-cultured to $1 \times 10^8$ to $9 \times 10^{10}$ cells/mL.

It may be preferable that the agent for increasing a plant functional component content comprises a biosurfactant.

It may be preferable for the agent for increasing a plant functional component content that the metabolism is a metabolism under a condition of a temperature from 20 to 30° C.

It may be preferable that the agent for increasing a plant functional component content is used as a spraying agent or an immersion agent for contacting with a plant stem, leaf, or root, or a soil injection agent.

It may be preferable for the agent for increasing a plant functional component content that the plant functional component is selected from a group consisting of polyphenols, amino acids, terpenoids and a combination thereof.

It may be preferable for the agent for increasing a plant functional component content that the amino acids are selected from a group consisting of proline, glutamic acid and γ-amino butyric acid.

It may be preferable that the agent for increasing a plant functional component content is used for Solanaceous plants, Cruciferous plants, Compositae plants, Chenopodiaceae plants.

Further the present invention relates to a method for manufacturing an agent for increasing a plant functional component content comprising a fatty acid metabolite, comprising a step for a fatty acid metabolism wherein a fatty acid with 4 to 30 carbon atoms is subjected to a proteobacterial metabolization under a dissolved oxygen concentration of 0.1 to 8 mg/L.

It may be preferable for the method for manufacturing an agent for increasing a plant functional component content that the fatty acid is liquid at a temperature of 20° C.

It may be preferable that the method for manufacturing an agent for increasing a plant functional component content comprises the step for the fatty acid metabolism performed in the presence of at least one type of mineral selected from Mg, P, Na and K.

It may be preferable for the method for manufacturing an agent for increasing a plant functional component content that the proteobacteria are pre-cultured proteobacteria.

It may be preferable for the method for manufacturing an agent for increasing a plant functional component content that the proteobacteria are proteobacteria pre-cultured to $1 \times 10^8$ to $9 \times 10^{10}$ cells/mL.

It may be preferable for the method for manufacturing an agent for increasing a plant functional component content that the agent for increasing a plant functional component content comprises a biosurfactant.

It may be preferable that the method for manufacturing an agent for increasing a plant functional component content comprises the step for the fatty acid metabolism performed under a condition of a temperature from 20 to 30° C.

It may be preferable for the method for manufacturing an agent for increasing a plant functional component content that the agent for increasing a plant functional component content serves as a spraying agent or an immersion agent for contacting with a plant stem, leaf, or root, or a soil injection agent.

It may be preferable for the method for manufacturing an agent for increasing a plant functional component content that the agent for increasing a plant functional component content serves as the agent to increase the plant functional component selected from a group consisting of polyphenols, amino acids, terpenoids and a combination thereof.

It may be preferable for the method for manufacturing an agent for increasing a plant functional component content that the agent for increasing a plant functional component content serves as the agent to increase the amino acid selected from a group consisting of proline, glutamic acid and γ-amino butyric acid.

It may be preferable for the method for manufacturing an agent for increasing a plant functional component content that the agent for increasing a plant functional component content is used for Solanaceous plants, Cruciferous plants, Compositae plants, Chenopodiaceae plants.

In the context of the present invention, an agent for increasing a plant functional component content refers here to an agent that can increase a functional component content in the plant by inducing the promotion of functional component formation and/or the suppression of decomposition of functional component in the plant.

Effects of the Invention

The agent for increasing a plant functional component content of the present invention can increase a content of the plant functional component by being adequately sprayed to the plant or injected into the soil without using stress cultivation conditions or plants with high content of the functional component. Further, according to the method for manufacturing an agent for increasing a plant functional component content of the present invention, the agent for increasing a plant functional component content that can increase a content of the plant functional component by being adequately sprayed to the plant or injected into the soil without using stress cultivation conditions or plants with high content of functional component can be produced.

EMBODIMENT FOR CARRYING OUT THE INVENTION

Figure 1:
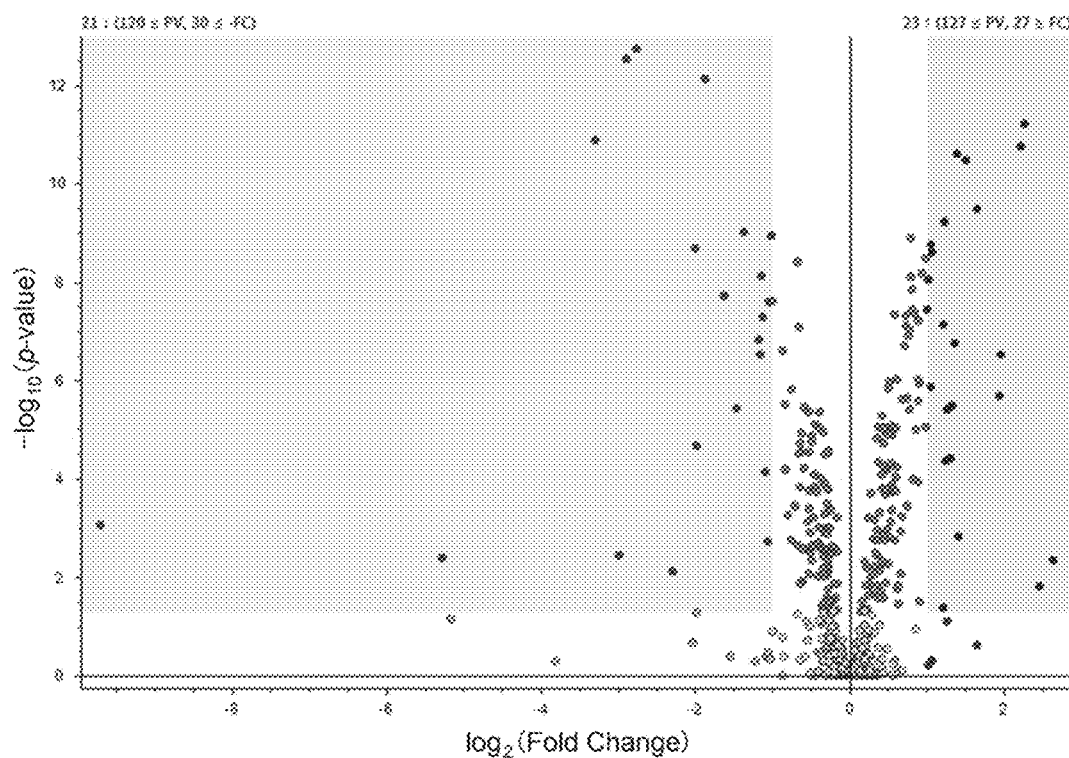
FIG. 1 is a volcano plot showing a comparison analysis among functional components when the agent for increasing a plant functional component content of the present invention was applied to Japanese mustard spinach.

An Agent for Increasing a Plant Functional Component Content

An agent for increasing a plant functional component content of the present invention is characterized in that it comprises a fatty acid metabolite obtainable by a metabolism of a fatty acid with 4 to 30 carbon atoms by proteobacteria under a dissolved oxygen concentration of 0.1 to 8 mg/L.

A fatty acid metabolite of the present invention can increase a content of the plant functional component by being contacted with a part of plant stems, leaves, or roots. Since the increase of the amount of the components that are same as the ones increased under a general stress cultivation condition is observed, it is appreciated that the fatty acid metabolite of the present invention includes a substance and/or a precursor of the substance which performs an action in plants, similar to the action which the molecules originally arising from environmental stresses and acting as a signal molecule in plants perform, by being absorbed in plants. Thus, the intrinsic plant function of stress tolerance can be strengthened by the fatty acid metabolite of the present invention. This leads a promotion of functional component formation and/or a suppression of decomposition of functional component in the plant, resulting in the increase of plant functional component in plants.

A metabolism in the context of the present invention involves performing a decomposition using a fatty acid with 4 to 30 carbon atoms by, for example, enzymes secreted via an endocrine or exocrine pathway by proteobacteria under a predetermined dissolved oxygen concentration. Examples include a method for culturing the proteobacteria in a culture media including the fatty acid in the context of the present invention under a predetermined dissolved oxygen concentration.

Proteobacteria have lipoxygenase (LOX) genes associated with a fatty acid metabolism and are capable of producing fatty acid metabolites.

The number of carbon atoms in the fatty acid to be used in the present invention is from 4 to 30, preferably 10 to 20. When the number of carbon atoms is less than 4, the melting point and/or boiling point of the fatty acid is low, so that it tends to become highly volatile at a culture temperature and can hardly remain in the culture media. When the number of carbon atoms is more than 30, the melting point and/or boiling point of the fatty acid is high, so that it tends to become a solid at a culture temperature and cannot be mixed with a culture media, resulting in the separation of the fatty acid from the culture media. However, it should be noted that the melting point of the fatty acid does not always depend on only the number of carbon atoms based on the number of hydrogen bonds.

The fatty acid to be used in the present invention is preferably a liquid fatty acid at a temperature from 20 to 30° C. in terms of its metabolism efficiency as well as to prevent a solidification in the culture media.

The fatty acid in the context of the present invention may be either a saturated fatty acid or a unsaturated fatty acid, or a mixture including both fatty acids. Further, a vegetable oil, a triglyceride form, or a free fatty acid may be used. Preferably, the fatty acid is a free fatty acid (monocarboxylic acid) in terms of its superior decomposition rate.

Exemplary examples of free fatty acids with 4 to 30 carbon atoms include for instance, butanoic acid (butyric acid), pentanoic acid (valeric acid), caproic acid, enanthic acid (heptylic acid), caprylic acid, pelargonic acid, capric acid, lauric acid, myristic acid, pentadecylic acid, palmitic acid, palmitoleic acid, margaric acid, stearic acid, oleic acid, vaccenic acid, linoleic acid, α-linolenic acid, γ-linolenic acid, eleostearic acid, arachidic acid, mead acid, arachidonic acid, behenic acid, lignoceric acid, nervonic acid, cerotic acid, montanic acid, and melissic acid. Preferably, the fatty acid is a fatty acid which has 10 to 20 carbon atoms such as capric acid, lauric acid, myristic acid, pentadecylic acid, palmitic acid, palmitoleic acid, margaric acid, stearic acid, oleic acid, vaccenic acid, linoleic acid, α-linolenic acid, γ-linolenic acid, eleostearic acid, arachidic acid, mead acid, or arachidonic acid. More preferably, the fatty acid is a fatty acid which has 18 carbon atoms such as oleic acid, linoleic acid, α-linolenic acid, or γ-linolenic acid.

Preferably, a fatty acid content in the culture media is 120 g/L or less, more preferably 100 g/L or less, still more preferably 60 g/L or less when the culture media containing the fatty acid is used. When the fatty acid content is over 120 g/L, emulsification of the fatty acid with water in the culture media may become difficult, deteriorating a metabolism efficiency or resulting in an inhibition of proteobacteria growth. Further, although the lower limit of the fatty acid content is not particularly limited, the fatty acid content is preferably 1.0 g/L or more.

Preferably, the culture media containing a fatty acid in the context of the present invention also contains a mineral component. Exemplary examples of mineral components include for instance, but not particularly limited to, a mineral component which is generally used for culturing microorganisms. Examples include for instance a component containing magnesium (Mg), phosphorous (P), sodium (Na), or potassium (K). These components can be used alone or in combination. Preferably two components, more preferably three components, among those mineral components may be used. A mineral component content in the culture media is not particularly limited, and can be adapted to the content used with a conventional method for culturing aerobic bacteria. The mineral component may be used preferably 15 g/L or less, more preferably 10 g/L or less in the aspect that it may cause salt damage when applied to the plant.

Proteobacteria which can be used in the context of the present invention are not particularly limited unless they provide a desirable effect of the present invention. Preferably, the proteobacteria are proteobacteria which have a suitable growth temperature (an optimum temperature) of from 10 to 40° C., more preferably 20 to 30° C. in terms of its fatty acid metabolism efficiency as well as growth efficiency.

Preferably, proteobacteria in the context of the present invention are pre-cultured proteobacteria, preferably, to the cell concentration at the end of pre-culture of $1\times10^8$ to $9\times10^{10}$ cells/mL, in such case the proteobacteria can have a superior fatty acid metabolism efficiency.

With the context of the present invention the metabolism is performed under a dissolved oxygen concentration of 0.1 to 8 mg/L. When the dissolved oxygen concentration is less than 0.1 mg/L, the proteobacteria activity tends to become low, resulting in a significantly low fatty acid metabolism efficiency. When the dissolved oxygen concentration is over 8 mg/L, the decomposition of the substrate fatty acid by oxygen in the culture media tends to be progressed in parallel with the metabolic process by proteobacteria, resulting in the reduction of a metabolic efficiency and the lower yield of metabolites as an active ingredient. The dissolved oxygen concentration may be more preferably 0.1 to 5 mg/L, still more preferably 0.1 to 4 mg/L. In this context, dissolved oxygen levels are values detected by using PO electrodes by a diaphragm galvanic electrode method or diaphragm polarographic method using a dissolved oxygen meter from HORIBA, Ltd.

The temperature during the metabolism can be adapted suitably according to the proteobacteria to be used, and is preferably from 20 to 30° C. in terms of a fatty acid metabolism efficiency.

With the context of the present invention, the agent for increasing a plant functional component content may include a biosurfactant in addition to the fatty acid metabolite. It helps for the fatty acid metabolite to become dispersible in water, which allows for better handleability of the agent for increasing a plant functional component content. In this context, the biosurfactant according to the present invention refers to a surfactant-like substance which the microorganism produces to take up the substances with high hydrophobicity and secretes from the cell. With the context of the present invention, the biosurfactant secreted by the proteobacteria can facilitate a dispersion of the fatty acid metabolite into water, so that it enables a spraying or soil injection of the agent for increasing a plant functional component content containing a fatty acid metabolite to be more efficient and easier. However, exemplary examples of biosurfactants are not limited to the biosurfactant which is produced by the proteobacteria in the context of the present invention upon the fatty acid decomposition, and the biosurfactants which are produced by other microorganisms may be used, in the other word, to the agent for increasing a plant functional component content of the invention may be further added the biosurfactant produced by other microorganisms. The biosurfactant has less toxicity to living organisms and high biodegradability compared to the synthetic surfactant, and thus more environment-friendly agents for increasing a plant functional component content would be obtained. Further, the biosurfactants which are produced by other microorganisms may be added during the fatty acid decomposition process using proteobacteria to facilitate the fatty acid decomposition by proteobacteria. The intake of the fatty acid by proteobacteria may be promoted.

The agent for increasing a plant functional component content of the present invention can induce an expression of stress responding genes, PR1, PR2 and PDF1.2 in the plant to which the agent for increasing a plant functional component content of the present invention is applied. As a result, for example, the development of cuticula or trichomes, enhanced formation of hairy roots, increased antioxidant formation, enhanced activity in the moisture evaporation prevention (for example, enhanced production of proline and the like, and thickening plant leaves), or thickening stems is observed in response to the environmental conditions or seasons for cultivation or depending on the kinds/varieties of plants or plant growth stages. Thus, the agent for increasing a plant functional component content increases a stress-resistance activity that plants intrinsically have. Therefore, the agent for increasing a plant functional component content can increase a content of the plant functional component without using stress cultivation conditions. Problems of a yield decrease or a reduction of resistance to insect pests, which may occur when the stress cultivation or plants with high content of functional component is used, can be prevented. According to the agent for increasing a plant functional component content, it is possible to enhance a stress-resistance activity of the plant and increase a functional component content by a simple treatment without changing the conventionally used cultivation method.

Exemplary examples of functional components whose content will be increased by the present invention include for instance, polyphenols, glycosides of the functional components, amino acids. Exemplary examples of polyphenols include for instance, chlorogenic acid, scopoletin, sinapinic acid, and sinapaldehyde. Exemplary examples of glycosides of the functional components include for instance, glucosinolates such as gluconasturtiin, and 2-methylpropyl glucosinolate, syringin, and luteorin glucoside. Exemplary examples of amino acids include for instance, proline, glutamic acid, γ-Aminobutyric acid, arginine, and tryptophan. More examples of functional components include for instance adenosine. The content of at least one functional component is increased by the agent for increasing a plant functional component content.

Exemplary examples of plants to which the present invention can be applied include for instance, but not particularly limited to, Solanaceae: plants, Cruciferous plants, Compositae plants, Fabaceae plants, Liliaceae plants, or Chenopodiaceae plants. For example, the agent for increasing a plant functional component content of the present invention may be applied to leaf vegetables such as lettuce, spinach, Japanese mustard spinach, potherb mustard (Mizuna), cabbage, and Chinese cabbage, baby leaves such as Romaine lettuce, beet, Japanese mustard spinach, spinach, potherb mustard (Mizuna), roquette, leaf mustard, kale, and chicory, herbs such as licorice, and ephedra, fruit vegetables such as tomato, eggplant, cucumber, bell pepper, paprika, okra, red pepper, and squash, beans such as soy bean, root vegetables such as welsh onion, onion, carrot, lotus root, and burdock.

The plant to which the agent for increasing a plant functional component content of the present invention is applied can be cultivated in any environment. For example, the plant may be planted in soil, or the plant may be soaked in a water culture medium. The agent for increasing a plant functional component content of the present invention may be applied to the plant by any method or process desired. For example, it may be applied as a spraying agent or an immersion agent for contacting with plant stems, leaves, or roots, or a soil injection agent. The present invention is particularly advantageous as it allows an increase of the content of plant functional component by merely, for example, spraying the agent for increasing a plant functional component content of the present invention, without any special equipment.

The present invention also relates to a plant which is cultivated by the aforementioned cultivation method, in which a content of the plant functional component has been increased. It is appreciated that such plants are beneficial as foodstuffs as well as materials for cosmetic or pharmaceutical products or supplements.

Manufacturing Method

A method for manufacturing an agent for increasing a plant functional component content containing a fatty acid metabolite of the present invention is characterized in that it comprises a step for a fatty acid metabolism wherein a fatty acid with 4 to 30 carbon atoms is subjected to a proteobacterial metabolization under a dissolved oxygen concentration of 0.1 to 8 mg/L.

The step for a fatty acid metabolism in the context of the present invention is a step wherein a decomposition is performed using a fatty acid with 4 to 30 carbon atoms by, for example, enzymes secreted via an endocrine or exocrine pathway by proteobacteria under a predetermined dissolved oxygen concentration. Examples include a method for culturing the proteobacteria in a culture media including the fatty acid in the context of the present invention under a predetermined dissolved oxygen concentration.

The dissolved oxygen concentration during metabolism in the step for the fatty acid metabolism in the context of the present invention is 0.1 to 8 mg/L. When the dissolved oxygen concentration is less than 0.1 mg/L, the proteobacteria activity tends to become low, resulting in a significantly low fatty acid metabolism efficiency. When the dissolved oxygen concentration is over 8 mg/L, the decomposition of the substrate fatty acid by oxygen in the culture media tends to be progressed in parallel with the metabolic process by proteobacteria, resulting in the reduction of a metabolic efficiency and the lower yield of metabolites as an active ingredient. The dissolved oxygen concentration may be more preferably 0.1 to 5 mg/L, still more preferably 0.1 to 4 mg/L. In this context, dissolved oxygen levels are values detected by using PO electrodes by a diaphragm galvanic electrode method or diaphragm polarographic method using a dissolved oxygen meter from HORIBA, Ltd.

The dissolved oxygen concentration in the context of the present invention may be adjusted according to, for example, a culture vessel, shaking speed, and an aeration volume.

The culture condition in the step for the fatty acid metabolism in the context of the present invention may be a similar condition to any of conventional conditions applied for culturing the conventional aerobic bacteria, other than the dissolved oxygen concentration, which is, in the present invention, within the predetermined range. Exemplary conditions include for instance a culturing method wherein an aerating cultivation is employed for 3 to 7 days by shaking a culture flask, or using a spinner flask or jar fermentor.

Preferably, the culture period may be a period during which, for example, an emulsification or a decomposition of the fatty acid is sufficiently employed, however, the culture period can be altered according to the shaking condition or amount of microorganisms to be employed. In this context, preferably the end point of the step for the fatty acid metabolism is determined by detecting the degree of decomposition of the fatty acid from, for example, the absorbance at wavelength 230 nm, thin layer chromatography (TLC), high performance liquid chromatography (HPLC), gas chromatography-mass spectrometry (GC-MS), or liquid chromatography-mass spectrometry (LC-MS).

The temperature in the step for the fatty acid metabolism in the context of the present invention may be adapted according to the proteobacteria to be used, and the step is preferably performed under the condition of the temperature of 20 to 30° C. in terms of a fatty acid metabolism efficiency.

The fatty acid and proteobacteria described herein in the context of the agent for increasing a plant functional component content of the present invention can be adapted for the fatty acid and proteobacteria for the step for the fatty acid metabolism in the context of the present invention.

In this context, a step for pre-culturing proteobacteria is not particularly limited, and may be any conventional methods for culturing aerobic bacteria. Preferably, after the preculture, only the proteobacterial cells may be collected by, for example, centrifugation, and subjected to the step for the fatty acid metabolism.

The agent for increasing a plant functional component content obtainable from a manufacturing method of the present invention may include a biosurfactant in addition to a fatty acid metabolite. In this context, the biosurfactant according to the present invention refers to a surfactant-like substance which the microorganism produces to take up the substances with high hydrophobicity and secretes from the cell. With the context of the present invention, the biosurfactant secreted by the proteobacteria can facilitate a dispersion of the fatty acid metabolite into water, allowing for better handleability of the agent for increasing a plant functional component content.

The agent for increasing a plant functional component content of the present invention may be obtained as a culture solution which is a mixture of, for example, culture media, substances secreted by proteobacteria containing a biosurfactant, and bacterial cells. This culture solution may be adapted for the agent for increasing a plant functional component content of the present invention as it is, or a supernatant obtained after a removal of bacterial cells from the culture solution by, for example, a centrifugation may be used for the agent for increasing a plant functional component content of the present invention. The agent for increasing a plant functional component content obtainable from a manufacturing method of the present invention may be applied to the plant. Although the culture solution can be used without dilution, preferably the culture solution may be used after a dilution because it may cause a shrinking of a plant part to which the culture solution is applied due to the osmotic effect caused by an evaporation of the solution and a concentrated mineral components at a high temperature. A dilution ratio is not particularly limited unless it provides a desirable effect of the present invention, and preferably it would be 10 to 1000 times dilution. In this context, the bacterial cells, once removed from the culture solution, may be cultured again in the culture media containing a fatty acid, and then the step for the fatty acid metabolism can be repeated.

EXAMPLES

The present invention will be illustrated in detail by way of the Examples below, although the present invention shall be not limited to those specific Examples.
Preparation of an Agent for Increasing a Plant Functional Component Content for Test
<Pre-Culturing Step>
To 1 L of water in the glass Erlenmeyer flask 20 g of peptone (Difco, enzymatic digest of protein), 1.5 g of magnesium sulfate heptahydrate, and 1.5 g of dipotassium hydrogenphosphate were dissolved, or, to 1 L of water 10 g of peptone (Difco, enzymatic digest of protein), 5 g of yeast extract, and 10 g of sodium chloride were dissolved. Each solution was autoclaved at 121° C. for 20 min to render it sterile, and after cooled to a room temperature, the suspension containing proteobacterial cells was inoculated. The mouth of the Erlenmeyer flask was sealed with a silicone closure. After inoculation, cells in the flask were cultured at 25±5° C. for 24 hours with shaking (120 rpm) using Bioshaker (Taitec, BR-23UM). The number of bacterial cells in the culture broth was $5\times10^8$ cells/mL. After the culturing, the culture broth was subjected to the centrifugation at 15,000× g, at the temperature of 20° C., and the bacterial cells were collected from the culture broth.
<Fatty Acid Metabolism Step>
To 1 L of sterilized water in the glass Erlenmeyer flask 12 g of linoleic acid (Wako, first grade), 1.5 g of magnesium sulfate heptahydrate and/or 1.5 g of dipotassium hydrogenphosphate, and the whole amount of the bacterial cells obtained from the pre-culturing step were added. The bacterial cells in the flask were cultured at 20° C. for 4 days with shaking (120 rpm) using Bioshaker (Taitec, BR-23UM) under the condition of a dissolved oxygen concentration of 4 mg/L. The decomposition of linoleic acid was determined through the analysis of the concentration of peroxylipid, which is one of the intermediate products from the degradation of linoleic acid, by measuring the absorbance at wavelength 230 nm using BioSpec-mini spectrophotometer (Shimadzu Scientific Instruments). After the culturing, the culture broth containing the bacterial cells was evaluated as an agent for increasing a plant functional component content for test as described below.
Effect of an Increase of the Content of Plant Functional Component in Tomato Example 1

54 of Tomato (cultivar "Reika") seedlings were planted with space of 60 cm between plants in the general farm field, and the solution of the agent for increasing a plant functional component content for test, which was 50 to 100 times diluted with water, was applied either by spraying (20 mL/plant) or watering it to soil (200 mL/plant) once every week. An untreated section was provided as a comparative section. Four weeks after the test started, 5 tomato fruits from the test section and 5 tomato fruits from the untreated section were harvested and the contents of plant functional component were evaluated. The fresh of a harvested tomato fruit was crushed, and the mixture was then filtered through silk cloth, and the resulting filtrate was dried by lyophilization and extracted with acetonitrile-water (1:1). The resulting components were evaluated by Maxis (Bruker Daltonics) for MS qualitative analysis and UltiMate 3000 HPLC system (Thermo Fisher Scientific) for LC/MS multivariate analysis.

The result shows that in the tomatoes which were treated with the agent for increasing a plant functional component content for test the contents of proline, glutamic acid and GABA (γ-Aminobutyric acid) were increased compared to the tomatoes collected from the comparative section. Proline gave rise to a 2.5 times higher peak intensity in mass spectrometry, glutamic acid gave rise to a 1.2 times higher peak intensity, and GABA gave rise to a 1.4 times higher peak intensity. Proline is known to be recognized as sweetness and its hydroxide derivative has a skin-beautifying effect. Further, GABA is reported to have an effect of, for example, blood pressure lowering. Therefore, both proline and GABA are plant functional components.

From the aforementioned results, it should be appreciated that the agent for increasing a plant functional component content of the present invention has a superior effect of an increase of the content of plant functional component. Further, the components, such as proline and GABA, whose contents were observed to be increased in Example of the present invention are those observed to be increased under a general stress cultivation condition due to a promotion of formation and/or a suppression of decomposition, and thus it is appreciated that those components were increased by a stress effect, which induces a stress-resistance effect of the agent for increasing a plant functional component content of the present invention. Therefore, it is appreciated that the effect of an increase of the content of plant functional component of the present invention is accomplished by a promotion of functional component formation in the plant, a suppression of decomposition of functional component formed in the plant, or a combination thereof.
Effect of an Increase of the Content of Plant Functional Component in Baby Leaves and Herbs Example 2

Figure 2:
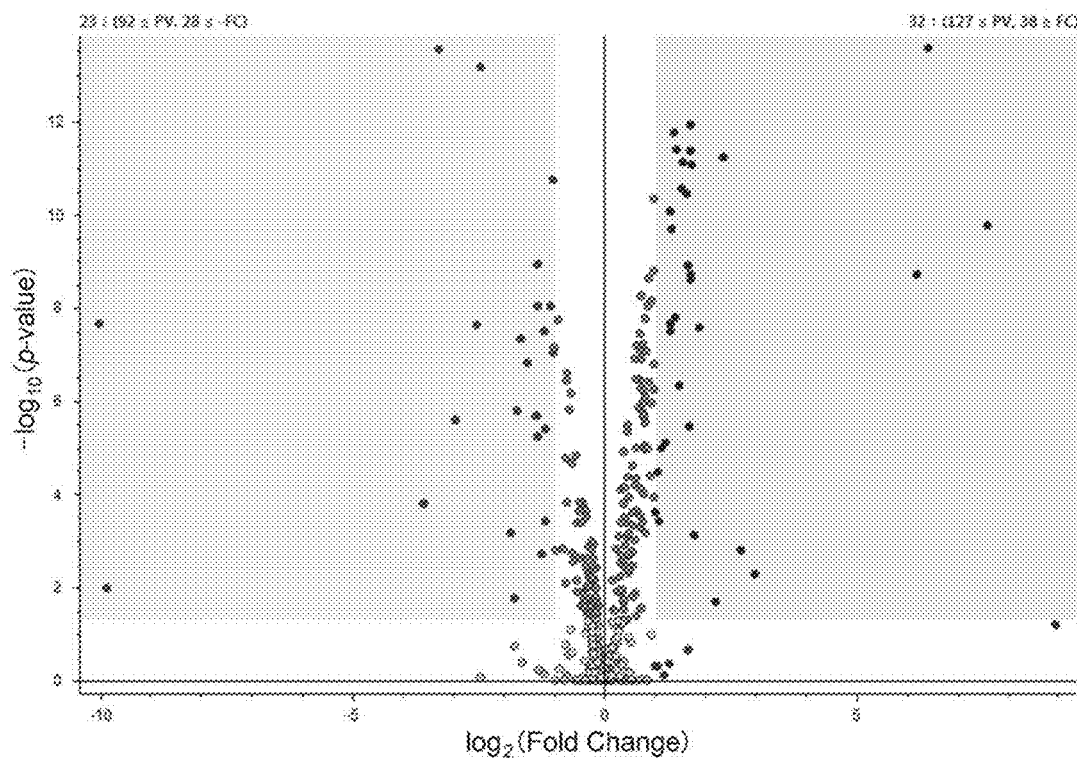
FIG. 2 is a volcano plot showing a comparison analysis among functional components when the agent for increasing a plant functional component content of the present invention was applied to potherb mustard.
Figure 3:
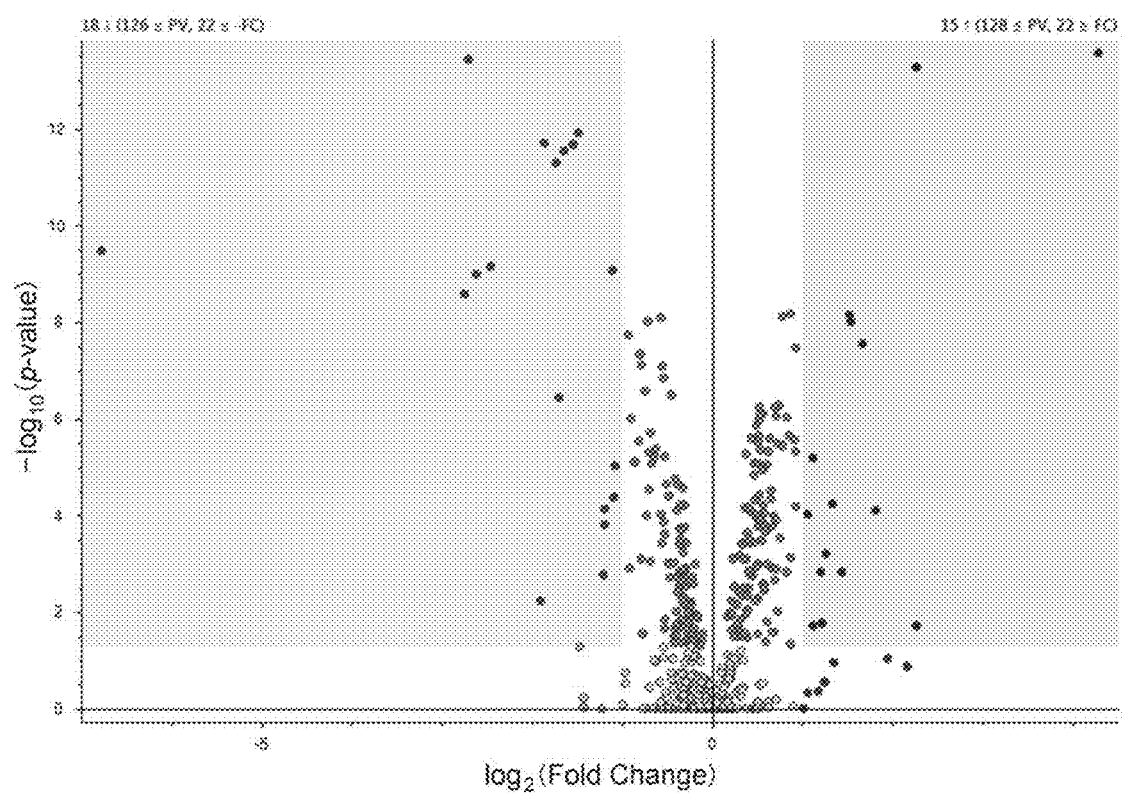
FIG. 3 is a volcano plot showing a comparison analysis among functional components when the agent for increasing a plant functional component content of the present invention was applied to roquette.

As a sample material, Japanese mustard spinach ("Komatsuna", *Brassica rapa* var. perviridis), potherb mustard ("Mizuna", *Brassica rapa* var. laciniifolia), and roquette were used. The seeds were sowed in culture soil (TAKII, & CO.LID, product name "Tanemaki-baido"), and within one week from sprouting the 100-times diluted solution with water of the agent for increasing a plant functional component content for test was applied using the watering to treat only the roots (underground part) of each plant. After sowing, the plants were cultivated till about the seedling stage, which was about 19 days after sowing. The edible part of each plant was lyophilized after freeze-crushing, and the resulting powder sample 30 mg was extracted with 2 mL of acetonitrile-water (1:1). To the extract as a sample was performed a principal component analysis by LC/MS for the components containing in the edible part. As a control, sample materials to which only water was applied using the watering were prepared, and the same analysis was performed. The results are shown in FIGS. 1, 2 and 3, and Table 1. Further, the morphology of each plant was examined.

FIGS. 1, 2 and 3 show a volcano plot illustrating the analysis of a detection amount of functional components in Japanese mustard spinach, potherb mustard or roquette after the agent for increasing a plant functional component content of the present invention was applied, compared to the detection amount before the agent for increasing a plant functional component content of the present invention was applied. In each volcano plot, the horizontal axis shows impact of fold change in quantitative alternation based on a log scale, the base 2 log of the fold change for the area of mass spectra corresponding to each component. The hatched part in each figure corresponds to the area in which there is a difference of 1 or more in log 2(fold change), indicating that there is observed a difference of 2 or more in the area of the corresponding components before and after the agent for increasing a plant functional component content of the present invention was applied. The hatched part on the upper left in each figure indicates that the area value of the corresponding component area after the agent for increasing a plant functional component content of the present invention was applied is twice or more compared to the area value before the agent for increasing a plant functional component content of the present invention was applied. In the context of the present invention, the areas having area value difference less than −2 times is considered, for convenience, that there is no significant difference before and after the agent for increasing a plant functional component content of the present invention was applied.

The vertical axis represents statistical evidence, a p-value, which is represented by the negative log 10-transformed p-values. When the p-value is less than 0.05, statistical significance is conventionally declared. Negative natural log of 0.05 is 1.3, and thus the hatched region in the figure is the region of 1.3 or higher on the vertical axis. Concretely, the hatched region on the left side of each of FIGS. 1 to 3 is a region in which a probability of events is high in that the component detected by mass spectra is increased significantly by applying the agent for increasing a plant functional component content of the present invention, and that component is present and is increased. It is appreciated that the number of the plots located in that region is the number of components which were specifically increased by applying the agent for increasing a plant functional component content of the present invention.

As shown in FIG. 1, there observed 21 components which were clearly increased in their amounts and variations on the volcano plot from LC/MS analysis of the extract of Japanese mustard spinach. As shown in FIG. 2, there observed 23 components which were clearly increased in their amounts and variations on the volcano plot from LC/MS analysis of the extract of potherb mustard. As shown in FIG. 3, there observed 18 components which were clearly increased in their amounts and variations on the volcano plot from LC/MS analysis of the extract of roquette.

TABLE 1

| plant varieties | component | MS intensity (amount of increase) |
|---|---|---|
| Japanese mustard spinach | chlorogenic acid | 2.7-fold |
| | scopoletin | 1.8-fold |
| | syringin | 1.4-fold |
| | tryptophan | 1.5-fold |
| | gluconasturtiin | 9.8-fold |
| roquette | adenosine | 6.5-fold |
| | arginine | 1.7-fold |
| | sinapaldehyde | 1.5-fold |
| | luteorin glucoside | 1.5-fold |
| | sinapinic acid | 1.9-fold |
| potherb mustard | sinapaldehyde | 2.1-fold |
| | 2-methylpropyl glucosinolate | 5.5-fold |

The representative functional components that were specifically increased in each plant and their amount of increase are shown in Table 1. The content of glucosinolates were significantly increased by a factor of 9.8 in Japanese mustard spinach treated with the agent for increasing a plant functional component content for test, and by a factor of 5.5 in potherb mustard treated with the agent for increasing a plant functional component content for test. Further, in roquette the content of luteorin glucoside is significantly increased by a factor of 1.5. The glucosinolates are glucosides containing sulfur and are known as functional components, among which is a glucosinolate precursor of isothiocyanate having an anti-cancer activity. The luteorin glucoside has been reported to exhibit anti-inflammatory and antioxidant activities. Further, the significant increase of polyphenols was observed. For example, the polyphenols were increased by a factor of 2.7 (chlorogenic acid) and by a factor of 1.8 (scopoletin) in Japanese mustard spinach treated with the agent for increasing a plant functional component content for test, by a factor of 1.5 (sinapaldehyde) and by a factor of 1.9 (sinapinic acid) in roquette treated with the agent for increasing a plant functional component content for test, and by a factor of 2.1 (sinapaldehyde) in potherb mustard treated with the agent for increasing a plant functional component content for test. Those polyphenols have been reported to exhibit an antioxidant effect or fat-burning effect as functional components. In addition, an increase of, for example, amino acids was also observed. It should be appreciated from those results that the agent for increasing a plant functional component content induces the promotion of different kinds of functional components formation and/or the suppression of decomposition of functional components contained in various plant species, enabling to increase the content of those components.

The morphology of each plant after cultivation was examined, and it was found that in potherb mustard the number of individuals that form acicular trichomes were increased. In roquette, it was found that red pigment was increased around the stems. It is known that the morphology changes of this sort are derived from the plant response to stresses, and thus, it should be appreciated that the agent for increasing a plant functional component content strengthens the plant function of stress tolerance, resulting in the increase of the content of plant functional component in plants.

Effect of an Increase of the Content of Plant Functional Component in Tomato Cultivated in Green House.

Example 3

36 of Tomato (cultivar "Reika") seedlings, which were grown until eighth leaves were expanded in the general farm field, were planted in the farm field. The seedlings were cultivated in three rows of ridges each covered with a mulching film in the farm field. In a test section, the solution of the agent for increasing a plant functional component content for test, which was 50 to 100 times diluted with water, was applied by watering it to soil (200 mL/plant) once every 2 weeks. An untreated section was provided as a comparative section. Both in a test section and in a comparative section, plants were watered as required based on the tomato seedling condition using sprinkling tube. Two months after the test started, 5 tomato fruits from the test section and 5 tomato fruits from the untreated section, the fruits being from the first cluster of flower buds which bloomed at the same time, were harvested in a random manner and the contents of plant functional components were evaluated. The fresh of a harvested tomato fruit was crushed, and the mixture was then filtered through silk cloth, and the resulting filtrate was dried by lyophilization and extracted with acetonitrile-water (1:1). The resulting components were evaluated by Q-EXACTIVE-FOCUS-LCMS (Thermo Fisher) for LC/MS multivariate analysis. The LC/MS was performed under the following conditions.

The LC/MS was performed using gradient elution and the gradient was established by introducing a mixture of a mobile phase A and a mobile phase B as the mobile phase for LC/MS, in which the mobile phase A was composed of a mixture of 0.1% formic acid and water and the mobile phase B was composed of a mixture of 0.1% formic acid and acetonitrile, at a flow rate of 0.3 mL/min, from mobile phase A: mobile phase B=98:2 (0 min, 2 min hold) to mobile phase A: mobile phase B=2:98 in 6 min (20 min total run time). The column used was an Acquity UPLC BEH $C_{18}$ (2.1 mm×150 mm, 1.7 μm, Waters Corporation).

The result shows that in the tomatoes which were treated with the agent for increasing a plant functional component content for test the contents of the functional components, including proline, GABA and glutamic acid, were increased. The increased representative functional components and their amount of increase are shown in Table 2.

TABLE 2

| component | | untreated | treated with metabolite | amount of increase |
|---|---|---|---|---|
| Sugar content | | 5.4% | 5.7% | +0.3% |
| proline peak area in MS chromatogram | RT 1.43 min $[M + H]^+$ 116.0709 | 261881 | 125627 | 2.1-fold |
| GABA peak area in MS chromatogram | RT 1.35 min $[M + H]^+$ 104.0708 | 902721 | 753711 | 1.2-fold |
| glutamic acid peak area in MS chromatogram | RT 1.37 min $[M + H]^+$ 148.0609 | 2115095 | 1787889 | 1.2-fold |
| aconitic acid peak area in MS chromatogram | RT 1.98 min $[M + H]^+$ 175.0238 | 321378 | 271055 | 1.2-fold |

The result shows that with the treatment by the agent for increasing a plant functional component content for test, the sugar content in tomato was increased, the accumulation of glutamic acid was promoted, and the decomposition of GABA was suppressed. Further, the content of proline, which is known to have a functionality of, for example, promotion of a collagen synthesis, was increased by a factor of 2.1. It should be appreciated from those results that the agent for increasing a plant functional component content has a remarkable effect on the promotion of functional components formation and/or the suppression of decomposition of functional components, providing a superior effect on the increase of the plant functional contents in the plant.

The above described results show that the agent for increasing a plant functional component content of the present invention and the agent for increasing a plant functional component content obtainable by the manufacturing method of the present invention have superior effect of increasing the content of plant functional components.

The invention claimed is:

1. An agent for increasing a plant functional component content comprising a fatty acid metabolite obtained by a metabolism of a fatty acid with 4 to 30 carbon atoms by proteobacteria under a dissolved oxygen concentration of 4 to 8 mg/L.

2. The agent for increasing a plant functional component content of claim 1, wherein the proteobacteria are pre-cultured proteobacteria.

3. The agent for increasing a plant functional component content of claim 2, wherein the pre-cultured proteobacteria are proteobacteria pre-cultured to $1 \times 10^8$ to $9 \times 10^{10}$ cells/mL.

4. The agent for increasing a plant functional component content of claim 1, wherein the plant functional component is selected from a group consisting of polyphenols, amino acids, terpenoids and a combination thereof.

5. The agent for increasing a plant functional component content of claim 4, wherein the amino acids are selected from a group consisting of proline, glutamic acid and γ-amino butyric acid.

6. The agent for increasing a plant functional component content of claim 1, wherein the fatty acid is a liquid at a temperature of 20° C.

7. The agent for increasing a plant functional component content of claim 1, wherein the metabolism is a metabolism in the presence of a mineral comprising at least one selected from the group consisting of Mg, P, Na and K.

8. The agent for increasing a plant functional component content of claim 1, wherein the agent for increasing a plant functional component content comprises a biosurfactant.

9. The agent for increasing a plant functional component content of claim 1, wherein the metabolism is a metabolism under a condition of a temperature from 20 to 30° C.

10. A method for manufacturing an agent for increasing a plant functional component content comprising a fatty acid metabolite, comprising a step for a fatty acid metabolism wherein a fatty acid with 4 to 30 carbon atoms is subjected to a proteobacterial metabolization under a dissolved oxygen concentration of 4 to 8 mg/L.

11. The method for manufacturing an agent for increasing a plant functional component content of claim 10, wherein the proteobacteria are pre-cultured proteobacteria.

12. The method for manufacturing an agent for increasing a plant functional component content of claim 11, wherein the proteobacteria are proteobacteria pre-cultured to $1 \times 10^8$ to $9 \times 10^{10}$ cells/mL.

13. The method for manufacturing an agent for increasing a plant functional component content of claim 10, wherein the agent for increasing a plant functional component content serves as the agent to increase the plant functional component selected from a group consisting of polyphenols, amino acids, terpenoids and a combination thereof.

14. The method for manufacturing an agent for increasing a plant functional component content of claim 13, wherein the agent for increasing a plant functional component content serves as the agent to increase the amino acid selected from a group consisting of proline, glutamic acid and γ-amino butyric acid.

15. The method for manufacturing an agent for increasing a plant functional component content of claim 10, wherein the fatty acid is liquid at a temperature of 20° C.

16. The method for manufacturing an agent for increasing a plant functional component content of claim 10, wherein the step for the fatty acid metabolism is performed in the presence of a mineral comprising at least one selected from the group consisting of Mg, P, Na and K.

17. The method for manufacturing an agent for increasing a plant functional component content of claim 10, wherein the agent for increasing a plant functional component content comprises a biosurfactant.

18. The method for manufacturing an agent for increasing a plant functional component content of claim 10, wherein the step for the fatty acid metabolism is performed under a condition of a temperature from 20 to 30° C.

19. The method for manufacturing an agent for increasing a plant functional component content of claim 10, wherein the agent for increasing a plant functional component content serves as a spraying agent or an immersion agent for contacting with a plant stem, leaf, or root, or a soil injection agent.

20. The method for manufacturing an agent for increasing a plant functional component content of claim 10 wherein the agent for increasing a plant functional component content is used for at least one member selected from the group consisting of Solanaceous plants, Cruciferous plants, Compositae plants, and Chenopodiaceae plants.

* * * * *